United States Patent [19]

Swinney

[11] Patent Number: 5,026,553
[45] Date of Patent: Jun. 25, 1991

[54] SWINNEY'S HAIR GROWTH FORMULA

[75] Inventor: Dale E. Swinney, 102 S. Ballentine, Du Quoin, Ill. 62832

[73] Assignee: Dale E. Swinney, Du Quoin, Ill.

[21] Appl. No.: 512,140

[22] Filed: Apr. 20, 1990

Related U.S. Application Data

[63] Continuation-in-part of Ser. No. 390,066, Aug. 7, 1989, abandoned.

[51] Int. Cl.$^5$ ................................................ A61K 6/00
[52] U.S. Cl. ...................................... 424/401; 424/70; 424/73; 424/195.1
[58] Field of Search ................ 424/401, 70, 73, 195.1

[56]   References Cited

U.S. PATENT DOCUMENTS

| 4,478,853 | 10/1984 | Chaussee | 424/358 |
| 4,551,330 | 11/1985 | Wagman | 424/59 |
| 4,670,255 | 6/1987 | Yoshizumi | 424/93 |

Primary Examiner—Thurman K. Page
Assistant Examiner—D. Gabrielle Phelan

[57]   ABSTRACT

A composition for treating Male Pattern Baldness of human beings. It can also be effective for women with naturally occuring hair loss problems. The mixture consists of vegetable oil, a mixture of 10% water (h2o) and 90% alcohol, and pure virgin olive oil. The composition in the form of a liquid mixture is applied to and massaged into the hair and/or scalp at least once in each twenty four hour period. Each application period should be for a maximum of eight to ten hours overnight. Also, the minimal period should be no less than fifteen minutes.

5 Claims, No Drawings

SWINNEY'S HAIR GROWTH FORMULA

This application is a continuation-in-part of Ser. No. 390,066 filed 08/07/89, and now abandoned.

SUMMARY OF INVENTION

The object of this invention is to stop hair loss due to Male Pattern Baldness and other naturally occuring human being hair loss. This invention will fertilize dormant hair root(s) which are not producing hair(s). As the roots absorb the mixture, the dormant root(s) are activated, resulting in new hair growth.

According to one aspect of this invention, a composition for for treating Male Pattern Baldness and/or other natural occuring human being hair loss, comprises a mixture of vegetable oil, a water and alcohol mixture, and pure olive oil.

Preferably, the composition comprises 90 to 95% by weight vegetable oil, 2 to 3% by weight olive oil, 2 to 3% by weight alcohol, and 1 to 2% by weight water (H2o).

Preferably, the protein comprises pure soybean oil and the composition may comprise 93% by weight pure soybean oil, 3.5% by weight pure olive oil, 2.5% by weight alcohol, and 1% by weight water (H2o).

According to another aspect of this invention, a method of treating Male Pattern Baldness and/or other naturally occuring human being hair loss comprises applying the composition according to said one aspect of this invention to the hair and/or scalp, and massaging the composition into the hair and/or scalp.

Preferably, the composition is applied to and massaged into the hair and/or scalp at least once during each twenty four period and each message is continued for at least five minutes.

One particularly suitable specific composition consists of 15.5 ounces of pure soybean oil, 0.25 ounce of pure virgin olive oils 0.20 ounce of alcohol, and 0.05 ounce of water (H2O).

The composition is manufactured by pouring the olive oil and alcohol and water into a 16 ounce bottle. The olive oil, alcohol, and water (H2O) stirred until thoroughly mixed. The soybean oil is added to the mixture and thoroughly stirred into a even consistency.

The composition which is in the form of a liquid is applied to the hair and/or scalp and is thoroughly massaged into the hair and scalp for a period of at least five minutes. It has been found to be beneficial for the composition to be applied and massaged into the hair and the scalp at least once each twenty four hour and preferably, the treatment is continued for at least 6 months or longer to obtain the most beneficial effects.

It has been found that the application of this composition promotes new hair growth on a human scalp.

I claim:

1. A composition consisting of 90 to 95% by weight soybean oil, 2 to 3% by weight olive oil, 2 to 3% by weight isopropyl alcohol, and 1 to 2% by weight water (H2O).

2. A composition according to claim 1, consisting of 93% by weight pure soybean oil, 3.5% by weight pure olive oil, 2.5% by weight isopropyl alcohol, and 1% by weight water (H2O).

3. A method of treating hair and/or scalps comprising applying the composition according to claim 1 to the hair and/or scalp, and massaging the composition into the hair and/or scalp.

4. A method according to claim 3, wherein the composition is applied to and massaged into the hair and/or scalp at least once during each 24-hour period and each massage being conducted for at least five minutes.

5. A method of manufacturing a composition suitable for treating Male Pattern Baldness and/or other naturally occuring human hair loss on a human scalp, the composition having the following constituents, by percentage of liquid volume of total ingredients:

pure soybean oil: 15.5 ounces
pure virgin olive oil: 0.25 ounce
alcohol: 0.20 ounce
water (H2O): 0.05 ounce said manufacturing method comprises the steps of: pouring the olive oil and the alcohol and the water into a 16 ounce bottle and thoroughly mixing: adding the soybean oil to the mixture and thoroughly stirring into an even consistency.

* * * * *